United States Patent [19]

Lukacs et al.

[11] Patent Number: 5,043,324
[45] Date of Patent: Aug. 27, 1991

[54] MACROLIDE COMPOUNDS

[75] Inventors: Gabor Lukacs; Catherine Duchatelle-Ruggeri, both of Paris; Alain Olesker; Li Ming, both of Gif-Sur-Yvette; Sylvie Bobillot, Chevreuse; Ton Thatthang, Montpellier, all of France

[73] Assignee: Adir et Compagnie, Neuilly-sur-Seine, France

[21] Appl. No.: 510,549

[22] Filed: Apr. 18, 1990

[30] Foreign Application Priority Data

Apr. 20, 1989 [FR] France ................. 89 05246

[51] Int. Cl.$^5$ ................. A61K 31/70; C07H 17/08
[52] U.S. Cl. ................. 514/30; 536/7.1
[58] Field of Search ................. 536/7.1; 514/30

[56] References Cited

U.S. PATENT DOCUMENTS

| 4,343,069 | 8/1982 | Sakakibara et al. | 536/7.1 |
| 4,468,511 | 8/1984 | Kirst et al. | 536/7.1 |

Primary Examiner—Elli Peselev
Attorney, Agent, or Firm—Gordon W. Hueschen

[57] ABSTRACT

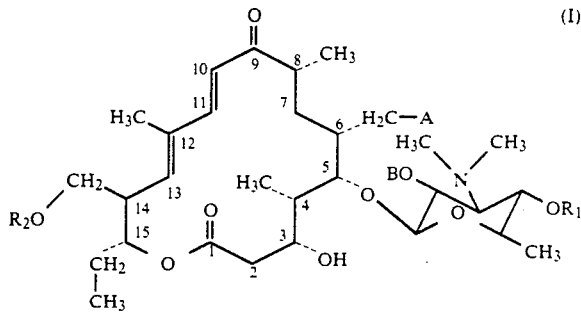

in which:
  B represents a hydrogen atom or a lower acyl group,
  A represents:
    a CH$_2$OH group, and in this case B represents a lower acyl group,
    a (CH$_2$)$_n$CN group,
    a (CH$_2$)$_n$CHO group,
    or a (CH$_2$)$_{(n-1)}$OH group
in which n is an integer between 1 and 6, R$_1$ and R$_2$ being defined in the description. The macrolide compounds are useful as antibacterial agents.

7 Claims, No Drawings

MACROLIDE COMPOUNDS

The present invention relates to new antibiotics of the macrolide family, to a process for preparing them and to pharmaceutical compositions containing them.

The requirements of therapeutics demand the constant development of new antibiotics, not only on account of the possibility of the appearance of new resistant strains, but also with the object of creating new molecules possessing improved activity in respect of both their threshold of efficacy and the breadth of their spectrum of action.

A large number of modifications of the tylosin ring-system have already been carried out in order to produce new advantageous antibiotics. Among the most recent, U.S. Pat. No(s). 4,528,369, 4,581,346 and 4,629,786 and European Patent Applications 0,103,465, 0,104,028, 0,154,495, 0,203,621 and 0,292,852 may be mentioned. However, none of these modifications has enabled a tylosin compound used in human therapy to be obtained More especially, the subject of the present invention is the products derived from tylosin of general formula (I):

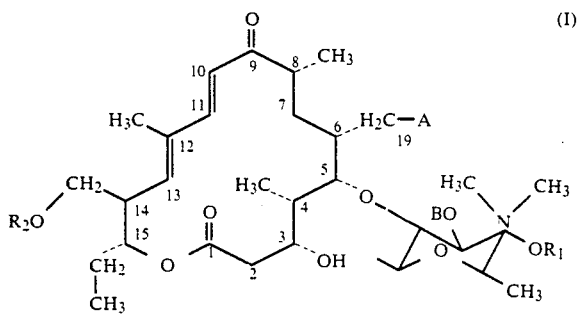

in which:
$R_1$ represents a hydrogen atom or a group:

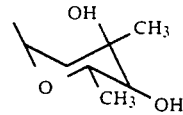

$R_2$ represents a hydrogen atom or a group:

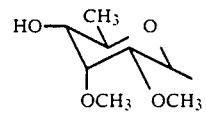

and in the case where $R_3$ represents a hydrogen atom, $R_1$ likewise represents a hydrogen atom,
B represents a hydrogen atom or a lower acyl group,
A represents:
a $CH_2OH$ group, and in this case B represents a lower acyl group, or:
a $(CH_2)_n CN$ group,
or a $-(CH_2)_n CHO$ group,
or a $-(CH_2)_{(+1)}OH$ group
in which n is an integer between 1 and 6, a lower acyl group being understood to be a group containing 1 to 5 carbon atoms.

The invention also encompasses the salts of the compounds of formula (I). Among acids which may be added to the compounds of formula (I) to form an addition salt, hydrochloric, hydrobromic, hydriodic, sulphuric, acetic, propionic, trifluoroacetic, maleic, malic, tartaric, methanesulphonic, ethanesulphonic, benzenesulphonic, ptoluenesulphonic, phosphoric, fumaric, citric, camphoric, stearic and ethylsuccinic acids, etc., may be mentioned by way of example.

The present invention also encompasses a process for preparing the compounds of formula (I), characterized in that the starting material used is a compound of formula (II):

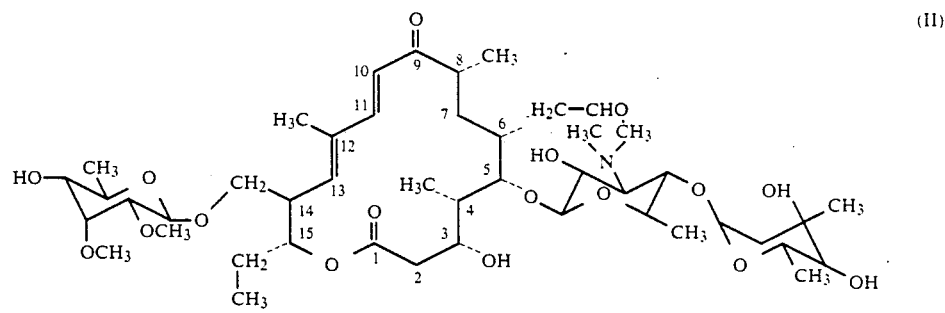

which, when $R_1$ represents a hydrogen atom in the compounds of formula (I) which it is desired to obtain, is subjected to the action of dilute hydrochloric acid of normality between 0.05 and 0.4, preferentially between 0.1 and 0.30 and preferentially between 0.15 and 0.25, at ambient temperature, to lead, after washing with a suitable organic solvent, rendering alkaline and extracting with a suitable organic solvent, to a compound of formula (II/A):

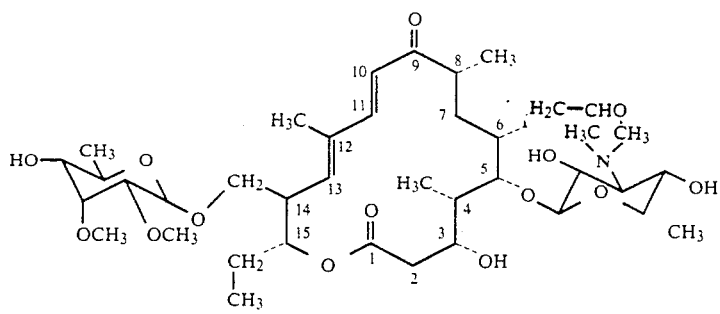
(II/A)

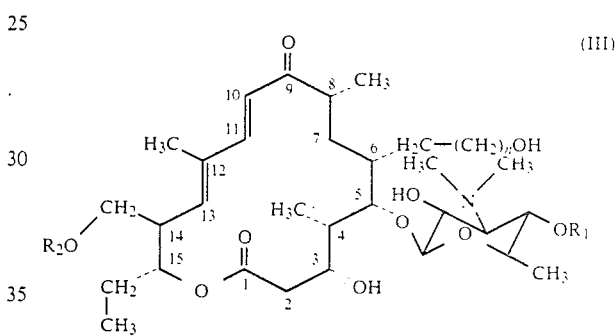
(III)

which compound of formula (II/A) is reacted, when R₂ represents a hydrogen atom in the compound of formula (I) which it is desired to obtain, with hydrochloric acid of normality between 0.25 and 0.75, preferentially between 0.3 and 0.7 and preferentially between 0.4 and 0.6, at a temperature preferentially between 30° and 100° C., preferentially between 50° and 90° C. and preferentially between 70° and 80° C., to lead, after washing with a suitable organic solvent, rendering alkaline and extracting with a suitable organic solvent, to a compound of formula (II/B):

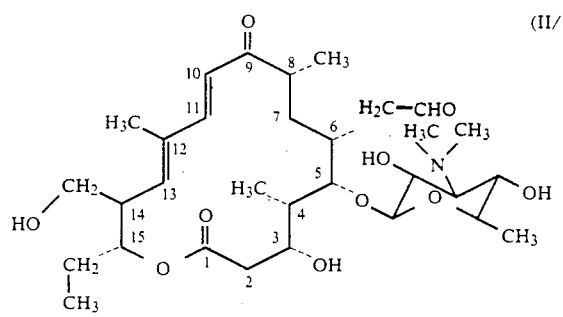
(II/B)

which compound of formula (II), (II/A) or (II/B), depending on the compound of formula (I) which it is desired to obtain, is subjected either:

1. to the action of an alkali metal mixed hydride in a lower aliphatic alcohol medium to obtain a compound of formula (III):

in which $R_1$ and $R_2$ have the same meaning as in formula (I) and n represents 1, which is subjected to the action of a lower carboxylic acid anhydride of formula Ac-OH, in which Ac represents a lower acyl group, preferentially at ambient temperature and preferentially under an inert atmosphere, to obtain a compound of formula (IV):

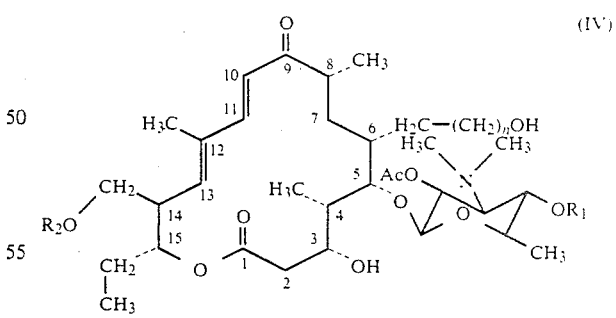
(IV)

in which Ac represents a lower acyl group, n is 1 and $R_1$ and $R_2$ have the same definition as in formula (I), said compound being a particular case of compounds of formula (I) for which B represents a lower acyl group and A represents a CH₂CH group, which compound is treated with tosyl chloride, which is added in small fractions, in the presence of 4-dimethylaminopyridine, to obtain, after purification, extraction and, if necessary, chromatography, if appropriate, a compound of formula (V):

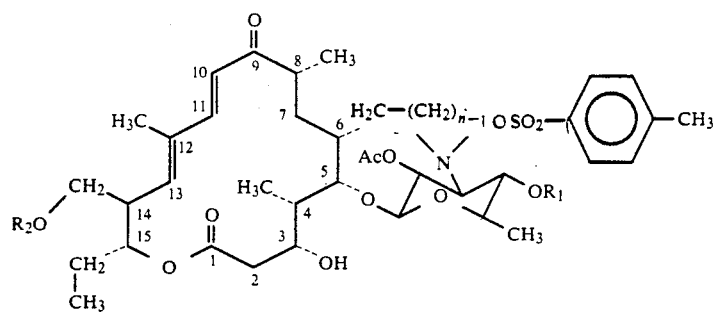

(V)

in which n, Ac, $R_1$ and $R_2$ have the same meaning as in formula (IV), which compound is treated with an alkali metal cyanide in the presence of a cryptand to obtain a compound of formula (VI):

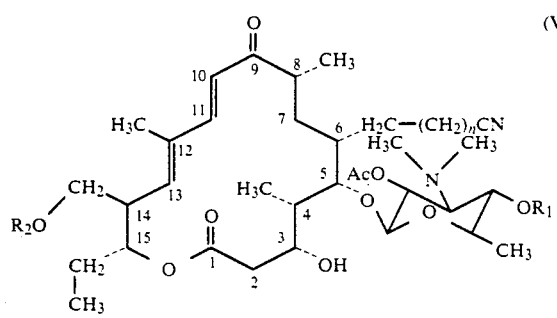

(VI)

in which n, Ac, $R_1$ and $R_2$ have the same meaning as in formula (IV), said compound being a particular case of compounds of formula (I) for which B represents a lower acyl group and A represents a $CH_2CN$ group, which compound is subjected to the action of methanol, to obtain a compound of formula (VIII):

which B represents a hydrogen atom and A represents a $CH_2CN$ group, which compound is treated with diisobutyl aluminium hydride, preferentially under an inert atmosphere, to lead to a compound of formula (VIII):

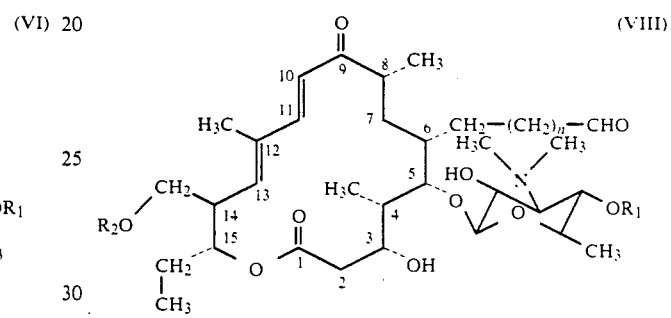

(VIII)

in which $R_1$ and $R_2$ have the same definition as in formula (I) and n represents 1, said compounds being a particular case of the compounds of formula (I) for which B represents a hydrogen atom and A represents a $CH_2$—CHO group, or:

2. to the action of (paratoluenesulphonyl)methyl chloride in the presence of an alkali metal tert.-butylate in a lower aliphatic alcohol, to lead, after purification by chromatography if appropriate, to a compound of formula (IX):

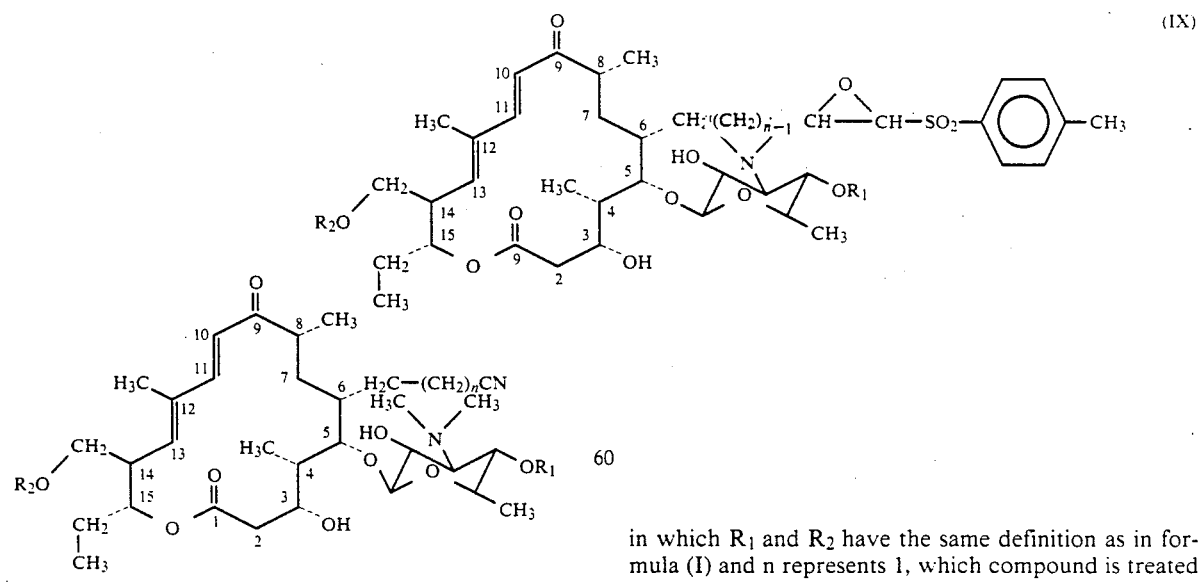

(VII)

(IX)

in which $R_1$ and $R_2$ have the same definition as in formula (I) and n represents 1, said compound being a particular case of the compounds of formula (I) for in which $R_1$ and $R_2$ have the same definition as in formula (I) and n represents 1, which compound is treated with an alkali metal mixed hydride in a dimethylformamide medium, preferentially with slight heating, to lead, after purification by chromatography if appropriate, to a compound of formula (X):

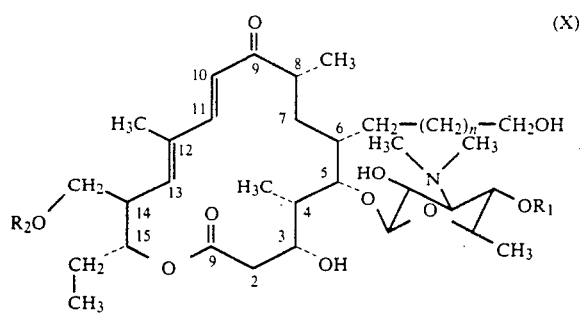

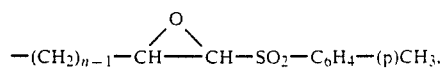

in which $R_1$ and $R_2$ have the same definition as in formula (I) and n represents 1, said compound being a particular case of the compounds of formula (I) for which A represents a $(CH_2)_2$—OH group and B represents a hydrogen atom, which compound is treated with pyridinium chlorochromate to obtain, after purification by chromatography if appropriate, a product of formula (VIII), which product, in its turn, can, if desired, be subjected, as indicated further above depending on the compound of formula (I) which it is desired to obtain either 3/ to the successive action of an alkali metal mixed hydride, a lower carboxylic acid anhydride, tosyl chloride in the presence of 4-dimethylaminopyridine, an alkali metal cyanide in the presence of a cryptand, methanol and then diisobutyl aluminium hydride to obtain, successively, the compounds of formula (III/A), (IV/A), (V/A), (VI/A), (VII/A) and (VIII/A), said derivatives being a particular case of the compounds of formula (III), (IV), (V), (VI), (VII) and (VIII) for which n represents 2, $R_1$ and $R_2$ having the same meaning as in formula (I) and Ac, where present, signifying a lower acyl group or 4/ to the successive action of (paratoluenesulphonyl)methyl chloride in the presence of alkali metal tert.-butylate, followed by alkali metal mixed hydride in the presence of dimethylformamide and then pyridinium chlorochromate to lead, successively, to the derivatives of formulae (IX/A), (X/A) and (VIII/A), said derivatives being a particular case of the compounds of formulae (IX), (X) and (VIII) for which n represents 2, $R_1$ and $R_2$ having the same meaning as in formula (I), which compound of formula (VIII/A), in its turn, is subjected, if appropriate, to one or two, three or four repeats of a treatment identical to those indicated in 3/ or 4/, to lead to a compound of formulae (III/B), (IV/B), (V/B), (VI/B), (VII/B) (VIII/B), (IX/B) and (X/B), said compounds being a particular case of the compounds of formulae (III), (IV), (V), (VI), (VII) (VIII), (IX) and (X) for which n represents 3, 4, 5 or 6, depending on whether the treatment indicated in 3/ or 4/ is repeated 1, 2, 3 or 4 times $R_1$ and $R_2$ having the same meaning as in formula (I) and Ac, where present, signifying a lower acyl group, which compounds are purified, if appropriate, by chromatography on a silica column with the aid of a suitable solvent mixture, and which can, if desired, be converted to a salt with a pharmaceutically acceptable acid.

The compounds of formula (V) and the compounds of (IX) and more generally the compound formula of formula (I) for which A represents a —$(CH_2)_nOSO_2$—$C_5H_4$—(p)$CH_3$ group and B represents an acetyl group, or A represents $$-(CH_2)_{n-1}-CH\overset{O}{\overline{\qquad}}CH-SO_2-C_6H_4-(p)CH_3.$$

n being between 1 and 6, are new and constitute part of the invention in the same way as the compounds of formula (I) for which they are synthesis intermediates.

The compounds of formula (I) possess advantageous pharmacological properties.

In particular, these compounds are active against gram+cocci and gram−cocci, gram+bacilli (clostridia), certain gram−bacilli, Haemophilus (e.g. *Haemophilus influenzae*), *Neissia gonorrhoeae*, Brucella, Bordetelella, anaerobic bacteria, mycoplasmata, rickettsiae and miyagawanellae (Chlamydia), spirochetes, protozoa and certain dermofungi.

More especially, the compounds of formula (I) possess very good antibiotic activity against pneumococci, staphylococci and streptococci. This spectrum of activity makes the compounds of formula (I) especially advantageous in the treatment of a large number of conditions; among these, it is possible to mention, by way of example, pneumococcal infections such as bronchiti, brucellosis and diphtheria, gonococcal infection, pneumonia, streptococcal infections such as acute angina, otitis, scarlet fever, sinusitis, staphylococcal infections such as staphylococcal septicemia, anthrax, erysipelas, pyoderma, acute staphylococcal infections bronchopneumonia and pulmonary suppurations.

In addition, the compounds of the present invention, by virtue of their structure, are likely to prove advantageous on account of their lack of hepatic or gastrointestinal toxicity, and this distinguishes them favourably from other families of antibiotic compounds.

The subject of the present invention is also pharmaceutical compositions containing the products of formula (I) or one of their addition salts with a pharmaceutically acceptable acid, alone or in combination with one or more pharmaceutically acceptable, non-toxic, inert vehicles or excipients.

Among the pharmaceutical compositions according to the invention, those which are suitable for oral, parenteral, nasal, rectal, perlingual, ocular or respiratory administration may be mentioned more especially, and in particular injectable preparations, aerosols, eye or nose drops, simple or sugar-coated tablets, sublingual tablets, sachets, packets, gelatin capsules, sublingual preparations, bars, suppositories, creams, ointments, skin gels, and the like.

The pharmaceutical compositions according to the invention may also be presented in the form of a lyophilized powder for dissolution at the time of use in a suitable solvent, in particular pyrogen-free sterile water.

The dosage varies according to the patient's age and weight, the administration route and the nature of the therapeutic indication and of any associated treatments, and ranges between 1 centigram and 4 grams per dose or per application.

The examples which follow illustrate the invention and in no way limit the latter.

The $^{13}C$ and $^1H$ nuclear magnetic resonance spectra were recorded using TMS as internal reference.

The starting material used in the synthesis of the compounds of formula (I) is tylosin, which is known in the literature.

EXAMPLE 1: 2'-ACETYL-20-DIHYDROTYLOSIN

STAGE A: 20-DIHYDROTYLOSIN 0.916 g (0.01 mole) of tylosin are dissolved in methanol. 0.037 g (0.014 mole) of sodium borohydride is added in small portions, with stirring an at ambient temperature, in the course of about on hour. Stirring is continued for three hours at ambient temperature. The mixture is evaporated to dryness and the residue is taken up in water and extracted 3 times with chloroform. The extract is dried over calcium chloride. The dried extract is filtered and the chloroform is evaporated on a water bath under vacuum.

STAGE B: 2'-ACETYL-20-DIHYDROTYLOSIN 0.29 g (0.3×10 mole) of 20-dihydrotylosin obtained in stage A are dissolved in 20 ml of anhydrous acetone. 0.001 mole of acetic anhydride are added and the mixture is stirred overnight at ambient temperature under an atmosphere of nitrogen. The mixture is evaporated. The residue is taken up in water saturated with sodium chloride and extracted with methylene chloride The organic phase is recovered, dried over sodium sulphate and evaporated on a water bath under vacuum. The product is purified by plate chromatography (eluent mixture: methylene chloride, methanol, ammonia 20/1/0.05).

Yield: 50%
Spectral characteristics:
Nuclear magnetic resonance: $^{13}C$ ($\delta$ppm):
204: $C_9$
74: $C_1$
69: (C=O) acetate
25 Mass: FAB [M-H]$^+$:961

EXAMPLE 2: 19-CYANOMETHYL-19-DEFORMYL-2'-ACETYLTYLOSIN

STAGE A: 20-O-PARATOLUENESULPHONYL-20-HYDRO-2'-O-ACETYLTYLOSIN 0.106 g (1.1×10$^{-4}$ mole) of 20-dihydro-2'-acetyltylosin obtained in Example 1 are dissolved in the presence of traces of 4-dimethylaminopyridine in 3 ml of dichloromethane and 0.3 ml of pyridine. 0.03 g (1.57×10$^{-4}$ mole) of tosyl chloride is added at ambient temperature under argon. After stirring for three hours, 0.018 g (1.1×10$^{-4}$ mole) of tosyl chloride is added. After stirring for 17 hours, a further 2 mg of tosyl chloride are added. After stirring for 22 hours, 0.2 ml of methanol is added. The mixture is then extracted with a water-sodium bicarbonate/methylene chloride (50/50) mixture, the extract is dried over sodium sulphate and the product is purified by flash chromatography (eluent: methylene chloride, methanol, ammonia 20/1/0.05).

Yield: 60%
Spectral characteristics:
Mass spectrometry: FAB [M-H]$^+$:1115
Nuclear magnetic resonance:
$^1H$ NMR
$\delta = 1.75$ ppm, singlet 3H $C_5H_4$—$CH_3$
$\delta = 7.05$-7.28 ppm 4H aromatic
$^{13}C$ NMR
$\delta = 203$ ppm $C_9$
$\delta = 174$ ppm $C_1$
$\delta = 169$ ppm (COO) acetate
$\delta = 29.3$ ppm $CH_3$—$C_6H_4$

STAGE B: 19-CYANOMETHYL-19DEFORMYL-2'-ACETYL-TYLOSin 0.035 g (0.53×10$^{-3}$ mole) of potassium cyanide and 0.217 g (0.57×10$^{-3}$ mole) of crown ether (dicyclohexyl-18-crown-6) are dissolved in 5 ml of anhydrous acetonitrile under argon using sound A solution of 0.5 g (0.45×10$^{-3}$ mole) of 20-O-paratoluenesulphonyl-20-hydro-2'-O-acetyltylosin obtained in stage A in 4 ml of acetonitrile is then added dropwise and with stirring. Stirring is continued overnight at ambient temperature. The reaction mixture is evaporated and the residue is purified on a silica column (eluent: $CH_2Cl_2$/MeOH/N-H$_4$OH-30/1/0.05)

$\alpha D$: $-62.4°$
Mass spectrometry: FAB [M-H]$^-$:970
Nuclear magnet resonance $^{13}C$ ($\delta$ppm):
$^1H$ NMR
2.1 ppm, singlet 3H $C_0$—$CH_3$
$^{13}C$ NMR
$\delta = 203$ ppm, $C_9$

EXAMPLE 3: 19-CYANOMETHYL-19-DEFORMYLTYLOSIN 0.97 g (1 millimole) of 19-cyanomethyl-19-deformyl-2'-acetyltylosin obtained in Example 2 is dissolved in 15 ml of methanol. The solution is stirred for 4 hours at ambient temperature. The reaction mixture is evaporated and the residue is extracted with twice 10 ml of chloroform. The organic phases are combined. The combined phases are dried over sodium sulphate, filtered and evaporated.

Yield: 90%
Spectral characteristics:
Mass spectrometry: FAB [M-H]$^-$928
Nuclear magnetic resonance $^{13}C$ ($\delta$ppm):
$^{13}C$ NMR
$\delta = 203$ ppm, $C_9$

EXAMPLE 4: 19-FORMYLMETHYL-19-DEFORMYLTYLOSIN 0.93 g (1 millimole) of 19-cyanomethyl-19-deformyltylosin obtained in Example 3 are dissolved under argon in a mixture of methylene chloride/anhydrous toluene (1/1 V/V). While maintaining the temperature at $-20°$ C., 2 millimoles of diisobutylaluminium hydride are added slowly. The temperature is allowed to return to ambient temperature and stirring is continued for 3 hours. A saturated solution of ammonium chloride is added and the mixture is extracted three times with 10 ml of methylene chloride. The extracts are dried over sodium sulphate. The reaction mixture is filtered and the filtrate evaporated. The product is purified by flash chromatography (eluent methanol/methylene chloride/ammonia 9.5/90/0.5).

Yield: 70%
Spectral characteristics:
Mass spectrometry: FAB [M-H]$^-$:925
$^{13}C$ NMR
$\delta = 203$ ppm, $C_9$

EXAMPLE 5:
19-DEFORMYL-19-(2-HYDROXYETHYL)-TYLOSIN

STAGE A:
6-(3-PARATOLUENESULPHONYL-2,3-EPOXY)-PROPYL-6-DEFORMYLMETHYLTYLOSIN 3.36 g (4 mmoles) of tylosin and 820 mg (4 mmoles) of (paratolylsulphonyl)methyl chloride are dissolved in 32 ml of anhydrous tetrahydrofuran and 2.3 ml of tert.-butanol under nitrogen. The mixture is cooled in an ice bath 448 mg (4 mmoles) of potassium tert.-butylate are added. The reaction mixture is stirred at ambient temperature for 2 hours. Ether is added, the mixture is filtered and the filtrate is evaporated to dryness. The crude product is purified by flash chromatography on a silica column (eluent: methylene chloride/-methanol-/ammonia (20/1/0.05)).

Yield: 70%
Spectral characteristics:
Mass spectrometry FAB $[M-H]^+$:1085
Nuclear magnetic resonance [1H]:
$\delta = 2.5$ ppm, singlet, 3H, $C_6H_5-CH_3$

STAGE B:
19-DEFORMYL-19-(2-HYDROXYETHYL)-TYLOSIN 2.4 g of 6-(3-paratoluenesulphonyl-2,3-epoxy)propyl-6-deformylmethyltylosin obtained in the preceding stage are dissolved in 40 ml of dimethylformamide. 60 mg of sodium borohyride are added. The reaction mixture is stirred at a temperature of 80° C. for 90 minutes. The reaction mixture is evaporated to dryness and the residue is purified by flash chromatography (eluent: methylene chloride/methanol/ammonia 20/1/0.05)

Yield: 75%
Spectral characteristics:
Nuclear magnetic resonance:
$^{13}C$ NMR
$\delta = 203$ ppm, $C_9$
$\delta = 174$ ppm, $C_1$
$\delta = 129$ ppm, $CH_2O_4$

EXAMPLE 6:
19-DEFORMYL-19-FORMYLMETHYLTYLOSIN 35 mg of pyridinium chlorochromate are added to a solution of 100 of 3Å molecular sieve in methylene chloride. After 3 minutes 100 m of 19-deformyl-19-(2-hyroxyethyl)tylosin obtained in Example 5 are added. The reaction mixture is stirred at ambient temperature for 2 hours. Ethyl ether is added and the mixture is filtered. The filtrate is evaporated to dryness and the residue purified on a preparative plate (eluent: methylene chloride/methanol/ammonia).

Mass spectrometry: FAB $[M-H]^+$:931
Spectral characteristics:
Nuclear magnetic resonance:
$^{13}C$ NMR
$\delta = 203.5$ ppm, $C_9$
$\delta = 202.8$ ppm, $C_{21}$
$\delta = 174$ ppm, $C_1$

EXAMPLE 7:
19DEFORMYL-19-(2-HYDROXYETHYL)-DEMYCAROSYLTYLOSIN

STAGE A: DEMYCAROSYLTYLOSIN 4 g (0.004 mole) of tylosin base are stirred in 80 ml of 0.2 N hydrochloric acid for 4 hours at ambient temperature. The reaction mixture obtained is washed with dichloromethane, the aqueous phase is separated and its pH adjusted to 8.0. The aqueous phase is extracted with twice 120 ml of dichloromethane and the organic phases are combined, dried over sodium sulphate and evaporated. The residue consists of demycarosyltylosin.

Yield: 94%

STAGE B:
19-DEFORMYL-19(2-HYDROXYETHYL)-DEMYCAROSYLTYLOSIN

The title product is obtained by carrying out the procedure as in Example 5 but replacing tylosin by dycarosyltylosin in stage A.

Yield: 65%
Spectral characteristics:
Mass spectrometry: FAB $[M-H]^-$:789

EXAMPLE 8:
19-DEFORMYL-19-FORMYLMETHYL-DEMYCAROSYLTYLOSIN

The title product is obtained by carrying out the procedure as in Example 6 but replacing 19-deformyl-19-(2-hyroxyethyl)tylosin by 19deformyl-19-(2-hydroxyethyl)demycarosyltylosin.

Spectral characteristics:
Mass spectrometry FAB $[M-H]^-$787
Nuclear magnetic resonance:
$^{13}C$ NMR
$\delta = 204$ ppm, $C_9$
$\delta = 174$ ppm, $C_1$
$\delta = 203$ ppm, $C_{21}$

EXAMPLE 9:
19-DEFORMYL-19-(2-HYDROXYETHYL)-DEMYCAROSYLDEMYCINOSYLTYLOSIN

STAGE A:
DEMYCAROSYLDEMYCINOSYLTYLOSIN 5 g (0.0065 mmole) of demycarosyltylosin obtained in stage A of Example 7 are dissolved in 110 ml of 0.5 N hydrochloric acid and the solution is stirred for about hours at 75° C. The reaction mixture is washed with dichloromethane. The aqueous phase is recovered, the pH is adjusted to 8 and the phase is extracted twice with 120 ml of dichloromethane. The organic phase is dried over sodium sulphate and evaporated. The residue is chromatographed on silica gel (eluent $CH_2Cl_2/MeOH/NH_4OH/-10/1/0.05$) to obtain the expected product.

Yield: 20%

STAGE B:
19-DEFORMYL-19-(2-HYDROXYETHYL)-DEMYCAROSYLDEMYCINOSYLTYLOSIN

The title product is obtained by carrying out the procedure as in Example 5 but replacing tylosin by demycarosyldemycinosyltylosin.

Yield: 50%
Spectral characteristics:
Mass spectrometry: FAB $[M-H]^-$:614

EXAMPLE 10:
19-DEFORMYL-19-FORMYLMETHYL-DEMYCAROSYLDEMYCINOSYLTYLOSIN

The title product is obtained by carrying out the procedure as in Example 6 but replacing 19-deformyl-19-(2-hydroxyethyl)tylosin by 19-deformyl-19-(2-hydroxyethyl)demycarosyldemycinosyltylosin obtained in Example 9

Spectral characteristics:
Mass spectrometry FAB [M-H]$^+$:612
Nuclear magnetic resonance:
$^{13}$C NMR
$\delta=204$ ppm, $C_9$
$\delta=174$ ppm, $C_1$
$\delta=203$ ppm, $C_{21}$

EXAMPLE 11:
19-DEFORMYL-19-(3-HYDROXYPROPYL)-TYLOSIN

The title product is obtained by carrying out the procedure as in Example 5 but replacing tylosin by 19-deformyl-19-formylmethyltylosin obtained in Example 6.

Spectral Characteristics:
Mass Spectrometry: FAB [M-h]$^+$:947

EXAMPLE 12:
19-DEFORMYL-19-(2-FORMYLETHYL)TYLOSIN

The title product is obtained by carrying out the procedure as in Example 6 but replacing 19-deformyl-19-(2-hydroxyethyl)tylosin by 19-deformyl-19-(3-hydroxypropyl)tylosin obtained in the preceding Example.

Spectral characteristics:
Mass spectrometry : FAB [M-H]$^+$:945
Nuclear magnetic resonance:
$^{13}$C NMR
$\delta=203$ ppm, $C_9$
$\delta=174$ ppm, $C_1$

EXAMPLE 13:
19-DEFORMYL-19-(4-HYDROXY-n-BUTYL)-TYLOSIN

The title product is obtained by carrying out the procedure as in Example 5 but replacing tylosin by 19-deformyl-19-(2formylethyl)tylosin obtained in Example 12.

Spectral characteristics:
Mass spectrometry: FAB [M-H]$^-$:961

EXAMPLE 14:
19-DEFORMYL-19-(3-FORMYL-n-PROPYL)-TYLOSIN

The title product is obtained by carrying out the procedure as in Example 6 but replacing 19deformyl-19(2-hydroxyethyl)tylosin by 19-deformyl-19-(4-hydroxy-n-butyl)tylosin obtained in the preceding Example.

Spectral characteristics:
Mass spectrometry: FAB [M-H]$^-$:959
Nuclear magnetic resonance:
$^{13}$C NMR
$\delta=203$ ppm, 9
$\delta=174$ ppm, $C_1$

EXAMPLE 15:
19-DEFORMYL-19-(5-HYDROXY-n-PENTYL)-TYLOSIN

The title product is obtained by carrying out the procedure as in Example 5 but replacing tylosin by 19-deformyl-19-(3-formyl-n-propyl)tylosin.

Spectral characteristics:
Mass spectrometry: FAB [M-H]$^-$:975

EXAMPLE 16:
19-DEFORMYL-19-(4-FORMYL-n-BUTYL)-TYLOSIN

The title product is obtained by carrying out the procedure as in Example 6 but replacing 19-deformyl-19-(2-hydroxyethyl)tylosin by 19-deformyl-19-(5-hydroxy-n-pentyl)tylosin.

EXAMPLE 17:
2'-ACETYL-19-DEFORMYL-19-(2-HYDROXYETHYL)TYLOSIN

The title product is obtained by carrying out the procedure as in Example 1 but replacing tylosin, in stage A, by 19-formylmethyl-19-deformyltylosin obtained in Example 4 or 6.

Spectral characteristics:
Mass spectrometry FAB [M-H]$^-$:975
Nuclear magnetic resonance:
$^{13}$C NMR
$\delta=204$ ppm, 9
$\delta=174$ ppm, $C_1$
$\delta=169$ (CO=O—O) acetate

EXAMPLE 18:
19(2-CYANOETHYL)-19-DEFORMYL2'-ACETYL-TYLOSIN

The title product is obtained by carrying out the procedure as in Example 2 but replacing 20-dihydro-2'-acetyltylosin by 2'-acetyl-19-deformyl-19-(2-hydroxyethyl)tylosin obtained in Example 17.

Spectral characteristics:
Mass spectrometry: FAB [M-H]$^-$:984

EXAMPLE 19:
19-(2-CYANOETHYL)-19-DEFORMYLTYLOSIN

The title product is obtained by carrying out the procedure as in Example 3 but replacing 19-cyanomethyl-19-deformyl-2'-acetyltylosin by 19-(2-cyanomethyl)-19-deformyl-2'-acetyltylosin obtained in Example 18.

Spectral characteristics:
Mass spectrometry: FAB [M-H]$^-$:942

EXAMPLE 20:
2'-ACETYL-19-DEFORMYL-19-(3-HYDROXY-n-PROPYL)TYLOSIN

The title product is obtained by carrying out the procedure as in Example 1 but replacing tylosin in stage A by 19-(2-formylethyl)-19deformyltylosin obtained in Example 12.

Spectral characteristics:
Mass spectrometry: FAB [M-H]$^-$:989
Nuclear magnetic resonance:
$^{13}$C NMR
$\delta=204$ ppm, $C_9$
$\delta=174$ ppm, $C_1$

EXAMPLE 21: 19-(3-CYANO-n-PROPYL)-19-DEFORMYL-2'-ACETYLTYLOSIN

The title product is obtained by carrying out the procedure as in Example 2 but replacing 20-dihydro-2'-acetyltylosin by 2'-acetyl-19-deformyl-19-(3hydro-n-propyl)tylosin obtained in Example 20.
Spectral characteristics:
Mass spectrometry: FAB [M-H]+:1129

EXAMPLE 22: 19-(3-CYANO-n-PROPYL)-19-DEFORMYL-TYLOSIN

The title product is obtained by carrying out the procedure as in Example 3 but replacing 19-cyanomethyl-19-deformyl-2'-acetyltylosin by 19-(3-cyano-n-propyl)-19-deformyl-2'-acetyltylosin obtained in Example 21.
Spectral characteristics:
Mass spectrometry: FAB [M-H]+:956

EXAMPLE 23: STUDY OF THE ACTIVITY OF THE PRODUCTS OF FORMULA (I) AGAINST VARIOUS BACTERIAL STRAINS

Determination of the minimal inhibitory concentrations (MIC) is performed:
for staphylococci and enterococci (group D streptococci), in MEULLER HINTON agar or liquid medium;
for Haemophilus, non-D streptococci and *Neisseria gonorrhoeae*, determination of the MIC is performed according to the dilution method in cooked blood agar medium enriched with Polyvitex* mixture. Culturing is carried out in a $CO_2$-enriched atmosphere.

Reading of the MIC is performed after 18 hours' incubation at 37° C.

The products are tested in the concentration range from 0.125 to 256 mg/l (successive doubling dilutions). The minimal inhibitory concentrations are of the order of:
0.25 mg.ml$^{-1}$ for *Staphylococcus arueus*;
1 mg.ml$^{-1}$ for enterococci.

These studies collectively show the advantageous antibiotic activity of the product of the invention, in respect of both the intensity of its activity and also the breadth of its spectrum of action.

EXAMPLE 24: PHARMACEUTICAL COMPOSITION: TABLET

Tablets containing 75 mg of 19-deformyl-19-formylmethyltylosin.

| Preparation formula for 1000 tablets | |
| --- | --- |
| 19-Deformyl-19-formylmethyltylosin | 75 g |
| Wheat starch | 70 g |
| Corn starch | 60 g |
| Lactose | 75 g |
| Magnesium stearate | 9 g |
| Silica | 4 g |
| Hydroxypropylcellulose for 1000 tablets. | 7 g |

What is claimed is:
1. A compound of formula (I):

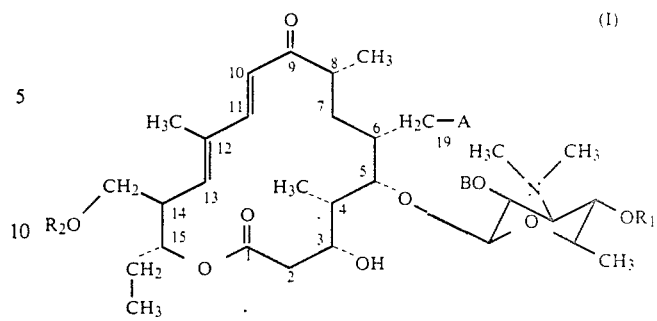

in which:
$R_1$ represents a hydrogen atom or a group:

$R_2$ represents a group:

B represents a hydrogen atom or a lower acyl group.
A represents:
a $(CH_2)N+1CN$
or a $—(CH_2)_n CHO$ group,
or a $—(CH_2)_{(n-1)}OH$ group
in which n is an integer of 1 to 5, inclusive and its addition salt with a pharmaceutically-acceptable acid.

2. A compound according to claim 1 in which A represents a $(CH_2)_{n+1}CN$ group and represents an integer of 1 to 5, inclusive and its addition salt with a pharmaceutically-acceptable acid.

3. A compounds according to claim 1 in which A represents a $(CH_2)_n CHO$ group, and n represents an integer of 1 to 5, inclusive and its addition salt with a pharmaceutically-acceptable acid.

4. A compound according to claim 1 in which A represents a $(CH_2)_{n+1}OH$ group, n represents an integer of 1 to 5, inclusive and its addition salt with a pharmaceutically-acceptable acid.

5. A compound according to claims 1 which is 19-formylmethyl-19-deformyltylosin and its addition salts with a pharmaceutically acceptable acid.

6. A pharmaceutical composition useful for combatting bacterial infections containing, as active principle, an effective antibacterial amount of at least one compound of claim 1 in combination with one or more pharmaceutically-acceptable excipients or vehicles.

7. A method for treating an animal afflicted with a bacterial infection susceptible thereto, comprising the step of administering to the said animal an effective antibacterial amount of a compound of claim 1.

* * * * *

UNITED STATES PATENT AND TRADEMARK OFFICE
CERTIFICATE OF CORRECTION

PATENT NO. : 5,043,324  Page 1 of 4

DATED : Aug. 27, 1991

INVENTOR(S) : Gabor Lukacs; Catherine Duchatelle-Ruggeri, Alain Olesker, Li Ming, Sylvie Bobillot, Ton Thatthang It is certified that error appears in the above-identified patent and that said Letters Patent is hereby corrected as shown below:

Title Page, [56] References Cited, U.S. PATENT DOCUMENTS: "4,343,069" should read -- 4,345,069. --.

Column 2, line 15; "$R_3$" should read -- $R_2$ --.

Column 2, line 23; ($^1$ 1)" should read -- (n+1) --.

Column 4, line 63; "$CH_2CH$" should read -- $CH_2OH$ --.

Column 5/6, right hand section of formula V:

reads " 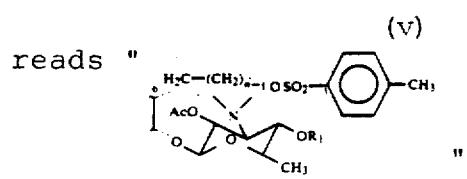 (V)    should read 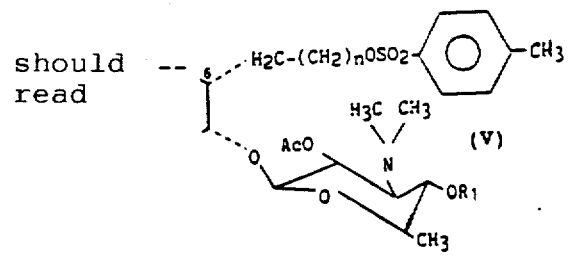 (V) --

Column 5, line 40; move "VII" to approximately line 50 near the right hand margin of Column 5.

Column 5/6, right hand section of formula IX:

reads " 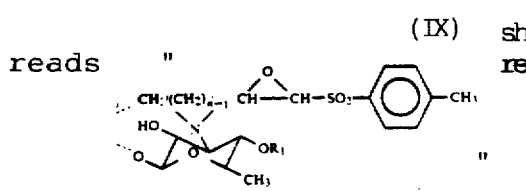 (IX)    should read 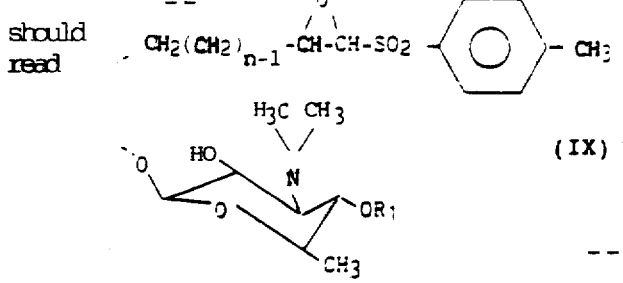 (IX) --

UNITED STATES PATENT AND TRADEMARK OFFICE
CERTIFICATE OF CORRECTION

PATENT NO. : 5,043,324

DATED : Aug. 27, 1991

INVENTOR(S) : Gabor Lukacs, Catherine Duchatelle-Ruggeri, Alain Olesker, Li Ming, Sylvie Bobillot, Ton Thatthang It is certified that error appears in the above-identified patent and that said Letters Patent is hereby corrected as shown below:

Column 8, line 25; "bronchiti," should read -- bronchitis --.
Column 9, approximately line 8; "on" should read -- one --.
Column 9, approximately line 17; "(0.3X10 mole)" should read
    -- (0.3 x $10^{-3}$ mold) --.
Column 9, approximately line 33; "74: $C_1$" should read -- 174: $C_1$ --.
Column 9, approximately line 34; "69:" should read -- 169 : --.
Column 10, approximately line 19; Column 10, following line 19,
    "αD: - 62.4°" insert the following as a separate line:
    -- Spectral characteristics: --.
Column 10, line 20; "[M-H]-:970" should read -- [M-H$^+$: 970 --.
Column 10, approximately line 23;     "2.1" should read -- δ = 2.1--.
Column 10, approximately line 40; "[M-H-928" should read
    -- [M-H]$^+$ : 928 --.
Column 10, line 61; "eluent methanol" should read
    -- eluent: methanol --.
Column 10, approximately line 65;"[M-H] -:925" should read
    -- [M-H]+ :925 --.
Column 10, line 65/66; after line 65 ending "925" insert the line
    -- Nuclear magnetic resonance: -- as a separate line.
Column 11, line 49; "100 m" should read -- 100 mg --.
Column 11, line 65; "19DEFORMYL" should read --19-DEFORMYL--.
Column 12, line 12; "-19(2-HYDROXYETHYL)-" should read
    -- -- -19-(2-HYDROXYETHYL)- --.
Column 12, line 21; "[M-H]- :" should read -- [M-H]+: --.
Column 12, line 28; "19deformyl" should read -- 19-deformyl --.
Column 12, approximately line 32; "[M-H]-787" should read
    -- [M-H]$^+$ : 787 --.
Column 12, approximately line 48; "hours" should read --27 hours--.
Column 12, approximately line 68;  "[M-H-: 614" should read
    -- [M-H]$^+$: 614 --.
Column 13, line 37; "[M-H]-:945" should read -- [M-H]$^+$: 945 --.

Column 13, line 58; "19deformyl-" should read -- 19-deformyl- --.

UNITED STATES PATENT AND TRADEMARK OFFICE
CERTIFICATE OF CORRECTION

PATENT NO. : 5,043,324

DATED : Aug. 27, 1991

INVENTOR(S) : Gabor Lukacs; Catherine Duchatelle-Ruggeri, Alain Olesker; Li Ming, Sylvie Bobillot, Ton Thatthang It is certified that error appears in the above-identified patent and that said Letters Patent is hereby corrected as shown below:

Column 13, line 59; "19(2-" should read -- 19-(2- --.
Column 13, line 63; "[M-H]-:959" should read --[M-H]$^+$ :959 --.
Column 13, line 66; "ppm, $_9$" should read -- ppm, $C_9$ --.
Column 14, approximately line 9; "[M-H]-:975"
    should read -- [M-H]$^+$: 975--.
Column 14, line 28; "[M-H]-: 975" should read --[M-H]$^+$: 975 --.
Column 14, line 31; "ppm, $_9$" should read -- ppm, $C_9$ --.
Column 14, line 36; "19(2-" should read -- 19-(2- --.
Column 14, line 44; "[M-H]-:984" should read --[M-H]$^+$: 984--.
Column 14, line 53; "[M-H]-:942 should read --[M-H]$^+$: 942 --.
Column 14, line 60; "19deformyltylosin" should read
    -- 19-deformyltylosin --.
Column 14, approximately line 63; "[M-H]-:989" should read
    -- [M-H]$^+$: 989 --.
Column 15, line 7; "(3hydro-n-" should read --(3-hydroxy-n- --.
Column 15, approximately line 44; "arueus;" should read --aureus;--.
Column 16, line 39; "(CH$_2$) N+1CN" should read --(CH$_2$)$_{n+1}$CN group --.

Column 16, line 41; "(n-1)" should read -- (n+1) --.
Column 16, line 45; "n-1" should read -- (n+1) --.
Column 16, line 45; "and represents" should read
    -- and n represents --
Column 16, line 48; "compounds" should read -- compound --.

UNITED STATES PATENT AND TRADEMARK OFFICE
CERTIFICATE OF CORRECTION

PATENT NO. : 5,043,324

DATED : Aug. 27, 1991

INVENTOR(S) : Gabor Lukacs; Catherine Duchatelle-Ruggeri, Alain Olesker, Li Ming, Sylvie Bobillot, Ton Thatthang It is certified that error appears in the above-identified patent and that said Letters Patent is hereby corrected as shown below:

Column 16, line 53; "group, n" should read -- group, and n --.

Column 16, line 56; "5. A" should read -- 5. The --.

Column 16, line 57; "salts" should read -- salt --.

Column 16, line 58; "pharmaceutically acceptable" should read -- pharmaceutically-acceptable --.

Signed and Sealed this

Twentieth Day of April, 1993

*Attest:*

MICHAEL K. KIRK

*Attesting Officer*  Acting Commissioner of Patents and Trademarks

UNITED STATES PATENT AND TRADEMARK OFFICE
CERTIFICATE OF CORRECTION

PATENT NO. : 5,043,324

DATED : Augsut 27, 1991

INVENTOR(S) : Gabor Lukacs, Catherine Duchatelle-Ruggeri, Alain Olesker, Li Ming, Sylvie Bobillot and Ton Thatthang It is certified that error appears in the above-identified patent and that said Letters Patent is hereby corrected as shown below:

Column 13, line 48; " (2formylethyl)" should read --(2-formylethyl) --.

Signed and Sealed this

Sixteenth Day of November, 1993

BRUCE LEHMAN

*Attest:*

*Attesting Officer*     Commissioner of Patents and Trademarks